United States Patent [19]
Huang

[11] Patent Number: 5,513,653
[45] Date of Patent: May 7, 1996

[54] ISOLATING DISEASEPROOF AND CONTRACEPTIVE HYGIENIC COVER

[76] Inventor: Ching-Hsiang Huang, No.60, Sec.2, Chung Shan Rd., Chung Ho City, Tapei Hsien, Taiwan

[21] Appl. No.: 426,660

[22] Filed: Apr. 21, 1995

[51] Int. Cl.$^6$ .............................. A61F 6/02; A61F 6/04
[52] U.S. Cl. ....................... 128/842; 128/844; 128/918
[58] Field of Search ................................... 128/842, 844, 128/918, 885, DIG. 25; 604/347–353

[56] References Cited

U.S. PATENT DOCUMENTS

| | | | |
|---|---|---|---|
| 4,588,397 | 5/1986 | Giacalone | 604/351 |
| 4,781,709 | 11/1988 | Grubman | 604/349 |
| 4,815,151 | 3/1989 | Ball | 604/349 |
| 5,409,475 | 4/1995 | Steer | 604/352 |

Primary Examiner—Michael A. Brown
Attorney, Agent, or Firm—Browdy and Neimark

[57] ABSTRACT

An isolating diseaseproof and contraceptive hygienic cover including a cover body and a ring member. The cover body is substantially hoof-shaped and has an opening at a middle lower portion thereof. The ring member is coaxially fixedly connected to peripheral wall of the opening. The cover body has a wall radially extending from the opening and rearward inclined. The wall of the cover body has a thickness gradually reduced from the peripheral wall of the opening to outer edge of the cover body. The hygienic cover is sheet-like and has greatly reduced area and volume, so that the manufacturing cost and time thereof are decreased. In use, the present hygienic cover is able to provide more reliable contraceptive and diseaseproof effect and can be more conveniently and quickly put on/taken off in a-simple manner without affecting a sexual activity.

15 Claims, 1 Drawing Sheet

ISOLATING DISEASEPROOF AND CONTRACEPTIVE HYGIENIC COVER

BACKGROUND OF THE INVENTION

The present invention relates to a contraceptive and diseaseproof hygienic implement, and more particularly to an isolating diseaseproof contraceptive hygienic cover which prevents the peripheral portions around private parts or sexual organs of people from being infected due to skin contact in the process of sexual intercourse.

In Chinese Utility Model No. 942249038, an isolating diseaseproof contraceptive hygienic pants disclosed, which includes a pants body and a separate contraceptive cap. The pants body is fixedly disposed with a fitting tube having a ring member, whereby the contraceptive cap can be fitted to the ring member to engage with the pants body. According to such arrangements, a user must first wear the pants body and then select a suitable contraceptive cap to fit with the pants body. While there are a number of disadvantages associated with such prior art, given as below:

1. It is difficult in manufacture of such contraceptive implement, resulting in high cost of time and labor.
2. It takes away the sensational thrills of sexual intercourse wearing such contraceptive.
3. To put on such implement before sexual intercourse and take it off thereafter takes time, spoiling the moods of love making activities to most people in one aspect; the contraceptive cap is apt to separate from the pants body when suffering violent action force and fails to achieve the diseaseproof and contraceptive effects.

Several other kinds of diseaseproof contraceptive implements are respectively disclosed in Chinese Utility Model No. 92230577.9, entitled "hygienic diseaseproof contraceptive pants", and No. 92227398.7, entitled "simple diseaseproof pants used in cooperation with phallus cap" and No. 92208772.5, entitled "contraceptive and diseaseproof safety cap". Each of the above cited contraceptive implements is composed of a pants body or a so-called private parts protective film and a contraceptive cap which is integrally formed with the pants body or adhered thereto. Although such contraceptive implements are able to prevent the private parts from being contacted and infected during sexual intercourse. It is relatively inconvenient to make use of such implements. For example, the integrally formed pants and contraceptive cap must be worn simultaneously and continuously and once they are worn, in case the contraceptive cap does not suit the user, the cap can not be solely replaced. In addition, the pants body is apt to stick to a user's skin when put on or taken off, so the user can not easily put on/take off and comfortably wear such contraceptive implements.

Furthermore, the aforesaid pants body has a unified thickness and is apt to be crimped in the process of use, rendering the user uncomfortable and resulting in the failure of diseaseproof and contraceptive effects.

To simplify the above cited prior arts and make the users comfortable in wearing and to prevent users from being infected with either venereal diseases or particularly from being attacked by bugs hidden in pubic hairs of human being that can be transmitted during sexual intercourse, the present inventor designs an improved diseaseproof contraceptive.

The present invention is safer than conventional condoms and is easier to put on or remove than pants-like contraceptive. The present invention has several advantages over a traditional condom in diseaseproof functions. The following situations can be effectively improved:

1. It can prevent bugs of all kinds hidden in pubic hairs of human being from transmitting between each other.
2. Venereal diseases caused by bacteria or viruses existing in the secretory liquid in female vagina or accumulated at the bottom end of a condom, still getting people infected, can be prevented.
3. Taking off a condom after sexual intercourse carelessly can result in infection of venereal diseases even though it is very effective in contraceptive function.
4. Infection of skin diseases of all kinds at the private parts of people can be prevented in the process of sexual intercourse.

SUMMARY OF THE INVENTION

It is therefore a primary object of the present invention to provide an isolating diseaseproof contraceptive hygienic cover which is manufactured at low cost and can be easily used while achieving reliable diseaseproof and contraceptive effect.

It is a further object of the present invention to provide the above hygienic cover which includes a cover body and a ring member fixedly connected with the cover body and made of relatively stiff material whereby a contraceptive cap can be firmly fitted on the ring member without departing therefrom so as to ensure the diseaseproof and contraceptive effect.

According to the above objects, the hygienic cover of the present invention includes a cover body and a ring member. The cover body is substantially hoof-shaped and has an opening at the middle lower portion thereof. The ring member is coaxially fixedly connected to peripheral wall of the opening. The cover body has a wall radially extending from the opening and rearward inclined. The wall of the cover body has a thickness gradually reduced from the peripheral wall of the opening to outer edge of the cover body.

In a preferred embodiment, the width between two symmetric lateral arch edges of the cover body is equal to inguinals of human body. The upper arch portion of the cover body extends to a lower portion of human hypogastrium, while a lower portion of the cover body such downward extends as to cover or partially cover human scrotum.

The cover body is made of resilient latex or foamed synthetic rubber material and the thickness of the wall of the cover body is reduced from the peripheral wall of the opening to the edge of the cover body, so that the cover body itself possesses a certain retaining strength and can keep standing upright without deforming even when suffering violent swinging force so as to achieve a reliable isolating effect.

The hygienic cover of the present invention is sheet-like and has greatly reduced area and volume, so that the manufacturing cost and time thereof are decreased. In use, the present hygienic cover is able to provide more reliable contraceptive and diseaseproof effect and can be more conveniently and quickly put on/taken off in a simple manner without affecting sexual activity.

The present invention can be best understood through the following description and accompanying drawings, wherein:

DETAILED DESCRIPTION OF THE PREFERRED EMBODIMENT

Figure 1:
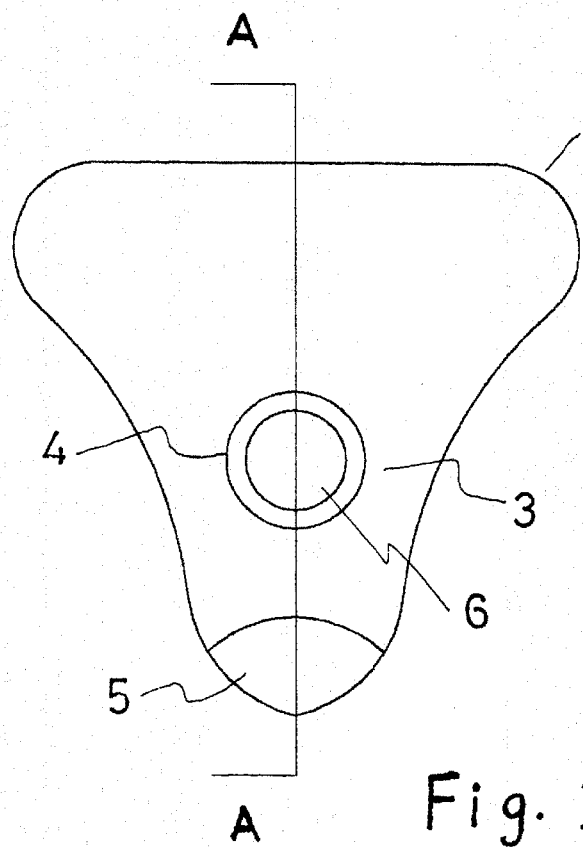
FIG. 1 is a front view of the present invention.
Figure 2:
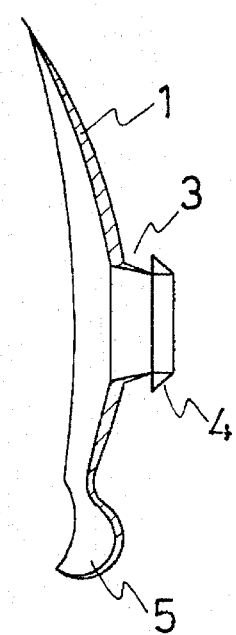
FIG. 2 is a sectional view taken along line A—A of FIG. 1.

Please refer to FIGS. 1 and 2. The contraceptive hygienic cover of the present invention includes a cover body 1 and a ring member 3. The cover body 1 is substantially hoof-shaped, having a wider upper end and a narrower lower end. That is, the cover body 1 has a tapered outline in general shape like an isosceles triangle having an acute included angle between the two equal sides, with well-rounded corners, and having indented equal sides. The cover body 1 is formed with an opening 6 at a middle or middle lower portion. The ring member 3 is integrally formed or fixedly connected to the peripheral wall of the opening 6.

The width between two symmetric lateral arch edges of the cover body 1 is equal to or less than the distance between the corresponding points of the inguinals of the human body. The upper arch portion of the cover body extends to a lower portion of the hypogastrium of human body, while the lower portion of the cover body extends downward to cover or partially cover the scrotum of human body.

The wall of the cover body 1 radially extends from the center of the opening 6 and is rearward inclined.

Generally, the angle contained by the center line of the opening 6 and the wall is within 50–89 degrees. The thickness of the wall of the cover body 1 is gradually reduced from the peripheral wall of the opening to the edge of the cover body 1. Therefore, the peripheral wall of the opening has a largest thickness within 8–2 millimeters, while the edge of the wall of the cover body has a smallest thickness within 2–0.01 millimeter. Alternatively, the thickness of the cover body can be substantially unified or slightly varied.

The ring member 3 is coaxially fixedly connected to the peripheral wall of the opening of the cover body 1 and axially protrudes therefrom. As seen in FIG. 2, the ring member 3 includes a lip 4 which extends outwardly from the generally cylindrical outer surface of the ring member 3 at its outermost end. A cross section of the lip 4, taken on the plane A—A of FIG. 2, shows a generally triangular shape. Generally, the surface of the lip 4 facing the cover body 1 (the rear face, also referred to below as the vertical rear face) is a planar annulus, the inner surface is cylindrical, and the outer surface is conical. The facing surface and the inner surface are thus substantially at right angles along any cross section, like section A—A, which passes through the central axis of the ring member 3. The cross-section of the ring member 3 is right triangle-shaped or substantially right triangle-shaped and is made of relatively stiff material, whereby the contraceptive cap can be firmly fixed to the ring member without departing therefrom or falling off. The plane in which the vertical rear face of the ring member 3 resides is spaced from the plane of the opening 6 of the cover body 1 by a distance within 5–20 millimeters.

The cover body 1 further has an arch convex portion 5 at the lower portion corresponding to the scrotum of human body, whereby when using the cover body 1, the convex portion 5 thereof can suitably receive the scrotum.

The dimension and shape of the above isolating contraceptive cover are determined according to the statistic data of related portions of human body. Several preferred specifications of the contraceptive covers can be manufactured to suit various users and achieve a comfortable feeling. The user can easily quickly put on the cover body without trouble. In addition, because the cover body is made of resilient latex film or foamed synthetic rubber material and the thickness of the wall of the cover body is reduced from the peripheral wall of the opening to the edge of the cover body, the cover body itself possesses a certain retaining strength and can keep standing upright without deforming. Furthermore, by means of the resilience of the latex and rubber material, the cover body is always adapted to the profile of the related portions of human body so as to effectively isolate and protect the same from being contacted and infected. Moreover, the cover body serves to buffer external force exerted on the scrotum or testes so as to protect the same.

The present invention has the following advantages over the prior arts:

1. It can guard a person against various kinds of venereal diseases.

2. It can prevent a condom from disengagement in the process of sexual intercourse.

3. It can prevent a person from being infected when removing a condom from the body.

4. It can get people relieved from a psychological burden of being infected by venereal diseases and help people fully enjoy the sentions of sexual intercourse.

5. It has two separate portions and condoms of various sizes can be selectively secured firmly to the ring member 3.

The above embodiment is only an example of the present invention and the scope of the present invention should not be limited to the example. Any modification or variation derived from the example should fall within the scope of the present invention.

I claim:

1. An isolating diseaseproof and contraceptive hygienic cover comprising a cover body and a ring member, said hygienic cover being characterized in that the cover body is substantially tapered in outline and has an opening at a middle lower portion thereof, the ring member being coaxially fixedly connected to the peripheral wall of the opening, the cover body having a wall radially extending from the opening and rearward inclined, the wall of the cover body having a thickness gradually reduced from the peripheral wall of the opening to outer edge of the cover body.

2. A hygienic cover as claimed in claim 1, wherein a width between two symmetric lateral arch edges of the cover body is equal to or less than a distance between corresponding points of inguinals-of human body.

3. A hygienic cover as claimed in claim 2, wherein an upper arch portion of the cover body extends to a lower portion of human hypogastrium, while a lower portion of the cover body so downward extends as to cover or partially cover human scrotum.

4. A hygienic cover as claimed in claim 3, wherein the cover body further has an arch convex portion at a lower portion thereof corresponding to the human scrotum.

5. A hygienic cover as claimed in claim 2, wherein the cover body further has an arch convex portion at a lower portion thereof corresponding to the human scrotum.

6. A hygienic cover as claimed in claim 1 wherein the cover body is made of resilient latex material.

7. A hygienic cover as claimed in claim 6, wherein the cover body further has an arch convex portion at a lower portion thereof corresponding to the human scrotum.

8. A hygienic cover as claimed in claim 1 wherein the cover body is made of foamed synthetic rubber material.

9. A hygienic cover as claimed in claim 8, wherein the cover body further has an arch convex portion at a lower portion thereof corresponding to the human scrotum.

10. A hygienic cover as claimed in claim 1 wherein an angle contained by a center line of the opening and the wall of the cover body is within 50–89 degrees.

11. A hygienic cover as claimed in claim 10, wherein the cover body further has an arch convex portion at a lower portion thereof corresponding to the human scrotum.

12. A hygienic cover as claimed in claim 1 wherein peripheral wall of the opening has a thickness within 8–2 millimeters, while the edge of the wall of the cover body has a thickness within 2–0.01 millimeter.

13. A hygienic cover as claimed in claim 12, wherein the cover body further has an arch convex portion at a lower portion thereof corresponding to the human scrotum.

14. A hygienic cover as claimed in claim 1 wherein the ring member has a lip which is right in cross section triangled-shaped in cross section and a plane in which a vertical rear face of the ring member resides is spaced from a plane of the opening of the cover body by a distance within 5–20 millimeters.

15. A hygienic cover as claimed in claim 14, wherein the cover body further has an arch convex portion at a lower portion thereof corresponding to the human scrotum.

* * * * *